(12) United States Patent
Franke et al.

(10) Patent No.: US 11,744,980 B2
(45) Date of Patent: Sep. 5, 2023

(54) EXHALATION VALVE ARRANGEMENT FOR A VENTILATOR APPARATUS WITH AN APPARATUS FOR RECEIVING A PRESSURE SENSOR

(71) Applicant: Hamilton Medical AG, Bonaduz (CH)

(72) Inventors: Karolin Franke, Chur (CH); Felix Breitruck, Buchs (CH)

(73) Assignee: Hamilton Bonaduz AG, Bonaduz (CH)

( * ) Notice: Subject to any disclaimer, the term of this patent is extended or adjusted under 35 U.S.C. 154(b) by 964 days.

(21) Appl. No.: 16/614,232

(22) PCT Filed: May 16, 2018

(86) PCT No.: PCT/EP2018/062795
§ 371 (c)(1),
(2) Date: Nov. 15, 2019

(87) PCT Pub. No.: WO2018/210958
PCT Pub. Date: Nov. 22, 2018

(65) Prior Publication Data
US 2021/0330925 A1    Oct. 28, 2021

(30) Foreign Application Priority Data

May 17, 2017   (DE) .................... 10 2017 208 349.2

(51) Int. Cl.
*A61M 16/20*   (2006.01)
*A61M 16/08*   (2006.01)

(52) U.S. Cl.
CPC ...... *A61M 16/206* (2014.02); *A61M 16/0858* (2014.02); *A61M 16/208* (2013.01)

(58) Field of Classification Search
CPC .... A61B 2560/0443; A61B 2562/0247; A61B 5/087; A61M 11/02; A61M 15/00;
(Continued)

(56) References Cited

U.S. PATENT DOCUMENTS 5,127,400 A   7/1992   Devries et al.
5,694,926 A   12/1997  DeVries et al.
(Continued)

FOREIGN PATENT DOCUMENTS

CN   101642597      2/2010
CN   102145201 A   10/2011
(Continued)

OTHER PUBLICATIONS

Search report for JP02019-563513 dated Feb. 17, 2022.
(Continued)

*Primary Examiner* — Annette Dixon
(74) *Attorney, Agent, or Firm* — TOLLEFSON IP (57) ABSTRACT

An exhalation valve arrangement (22) for a ventilation apparatus for artificial ventilation of patients is flow-capable in an exhalation flow direction (E) and encompasses:
  an upstream respiratory gas conduit (54) that extends along a first conduit path (K1) and is connected or connectable to a portion, coming from the patient, of the exhalation line;
  a downstream respiratory gas conduit (58) that extends along a second conduit path (K2) and is connected or connectable to a respiratory gas sink (U);
  a valve subassembly (63) which comprises a valve body (64) and a valve seat (66) and which is provided between the upstream and the downstream respiratory gas conduit (54, 58) in such a way that, in the context of a predetermined first respiratory gas overpressure in the upstream respiratory gas conduit (54) relative to the downstream respiratory gas conduit (58), it permits an expiratory respiratory gas flow from the upstream respiratory gas conduit (54) into the downstream respiratory gas conduit (58); and in the context of a predetermined second respiratory gas overpressure in the
(Continued)

downstream respiratory gas conduit (58) relative to the upstream respiratory gas conduit (54), it blocks a gas flow from the downstream respiratory gas conduit (58) into the upstream respiratory gas conduit (54).

Provision is made according to the present invention that the exhalation valve arrangement (22) comprises a bypass chamber (74) which communicates in terms of flow mechanics with the upstream respiratory gas conduit (54) and which extends, proceeding from the upstream respiratory gas conduit (54), into the region of the downstream respiratory gas conduit (58) and is embodied there for attachment of a gas pressure sensor (80).

23 Claims, 8 Drawing Sheets

(58) Field of Classification Search
CPC .............. A61M 16/00; A61M 16/0003; A61M 16/0051; A61M 16/0057; A61M 16/0066; A61M 16/0069; A61M 16/0078; A61M 16/0084; A61M 16/0096; A61M 16/022; A61M 16/024; A61M 16/04; A61M 16/0465; A61M 16/0468; A61M 16/0486; A61M 16/06; A61M 16/0666; A61M 16/08; A61M 16/0808; A61M 16/0816; A61M 16/0833; A61M 16/085; A61M 16/0858; A61M 16/0875; A61M 16/0883; A61M 16/1005; A61M 16/1045; A61M 16/1065; A61M 16/12; A61M 16/127; A61M 16/14; A61M 16/16; A61M 16/20; A61M 16/201; A61M 16/204; A61M 16/205; A61M 16/206; A61M 16/208; A61M 16/209; A61M 2016/0027; A61M 2016/003; A61M 2016/0033; A61M 2016/0039; A61M 2016/0042; A61M 2039/226; A61M 2039/2486; A61M 2202/04; A61M 2205/11; A61M 2205/16; A61M 2205/332; A61M 2205/3331; A61M 2205/3334; A61M 2205/3348; A61M 2205/3368; A61M 2205/42; A61M 2205/50; A61M 2205/6045; A61M 2205/7518; A61M 2206/11; A61M 2209/06; A61M 2230/432; A61M 2230/435; A61M 2230/50; A61M 39/00; A61M 39/223; A61M 39/24; A62B 18/10; A62B 9/02; A62B 9/027; F16K 1/36; F16K 1/42; F16K 1/44; F16K 1/523; F16K 11/04; F16K 11/044; F16K 15/14; F16K 15/144; F16K 15/148; F16K 25/00; F16K 27/0236; F16K 31/0624; F16K 31/0627; F16K 31/0655; F16K 31/0675; F16K 31/0693; F16K 31/082; F16K 39/02; F16K 39/022; F16K 41/10; F16K 47/02; F16K 7/14; F16K 7/17; Y10S 137/906; Y10S 137/908; Y10T 137/2544; Y10T 137/7781; Y10T 137/784; Y10T 137/7841; Y10T 137/7866; Y10T 137/7879; Y10T 137/789; Y10T 137/7904; Y10T 137/7905

See application file for complete search history.

(56) References Cited

U.S. PATENT DOCUMENTS

| | | | |
|---|---|---|---|
| 5,868,133 | A | 2/1999 | DeVries et al. |
| 5,881,722 | A | 3/1999 | DeVries et al. |
| 7,207,332 | B1 | 4/2007 | Lugtigheid |
| 10,500,367 | B2 | 12/2019 | Cewers |
| 2009/0139530 | A1 | 6/2009 | Landis et al. |
| 2010/0121212 | A1 | 5/2010 | Carlsson et al. |
| 2014/0305431 | A1 | 10/2014 | Holley et al. |
| 2016/0279376 | A1 | 9/2016 | Cewers |

FOREIGN PATENT DOCUMENTS

| | | |
|---|---|---|
| CN | 102274568 A | 12/2011 |
| CN | 202777378 U | 3/2013 |
| CN | 202859866 U | 4/2013 |
| CN | 203417393 | 2/2014 |
| CN | 203943996 | 11/2014 |
| CN | 105916539 A | 8/2016 |
| CN | 106334247 A | 1/2017 |
| EP | 1491227 | 12/2004 |
| EP | 2663354 | 8/2016 |
| GB | 1551226 | 8/1979 |
| WO | 2008/123831 | 10/2008 |

OTHER PUBLICATIONS

Reasons for refusal for JP02019-563513 dated Mar. 9, 2022.
Search Report issued for International application No. PCT/EP2018/062795 dated Jul. 19, 2018 (18 pages).
Chinese Office Action for 201880032112.1 dated Jan. 4, 2022.

EXHALATION VALVE ARRANGEMENT FOR A VENTILATOR APPARATUS WITH AN APPARATUS FOR RECEIVING A PRESSURE SENSOR

CROSS-REFERENCE TO RELATED APPLICATIONS

This application is the National Stage of International Application No. PCT/EP2018/062795, filed on May 16, 2018, which claims the benefit of German Application No. 10 2017 208 349.2, filed on May 17, 2017. The entire contents of both applications are hereby incorporated herein by reference.

The present invention relates to an exhalation valve arrangement for an exhalation line of a ventilation apparatus for artificial ventilation of patients, the exhalation valve arrangement being flow-capable in an exhalation flow direction and encompassing:

- an upstream respiratory gas conduit that extends along a first conduit path and is connected or connectable to a portion, coming from the patient, of the exhalation line;
- a downstream respiratory gas conduit that extends along a second conduit path and is connected or connectable to a respiratory gas sink, for example the external environment;
- a valve subassembly which comprises a valve body and a valve seat and which is provided between the upstream and the downstream respiratory gas conduit in such a way that, in the context of a predetermined first respiratory gas overpressure in the upstream respiratory gas conduit relative to the downstream respiratory gas conduit, it permits an expiratory respiratory gas flow from the upstream respiratory gas conduit into the downstream respiratory gas conduit; and in the context of a predetermined second respiratory gas overpressure in the downstream respiratory gas conduit relative to the upstream respiratory gas conduit, it blocks a gas flow from the downstream respiratory gas conduit into the upstream respiratory gas conduit.

Exhalation valve arrangements, such as the one described above, are used in ventilation apparatuses for at least assisted artificial ventilation of patients in order to generate a flow of respiratory gas which corresponds in terms of direction to the natural respiration cycles. The ventilation apparatuses usually comprise an inhalation line and an exhalation line, having an inhalation valve arrangement provided in the inhalation line and having an exhalation valve arrangement arranged in the exhalation line. Upon macroscopic consideration of the processes, the inhalation valve arrangement substantially permits only an inspiratory flow of respiratory gas toward the patient. Likewise upon macroscopic consideration, the exhalation valve arrangement substantially permits only an expiratory respiratory gas flow in the exhalation flow direction away from the patient.

Upon more detailed consideration of the exhalation valve arrangement, beyond mere opening and closing, further processes that are important for a ventilation process can occur therein, for example maintaining a residual flow-through opening at the valve subassembly toward the end of an exhalation process, to ensure that a positive end expiratory pressure (PEEP) is maintained in the exhalation line and thus also in the patient's lungs that communicate therewith in terms of flow.

The respiratory gas overpressures (first and second respiratory gas overpressure) that were recited initially need not either correspond in terms of magnitude or be at the same respiratory gas pressure level.

Because, in most known exhalation valve arrangements, the downstream respiratory gas conduit opens to the external environment constituting a respiratory gas sink of the ventilation apparatus that carries the exhalation valve arrangement, ambient pressure is usually imposed on the respiratory gas in the downstream respiratory gas conduit from its longitudinal end that opens toward the external environment. The first respiratory gas overpressure is therefore, as a rule, an overpressure in the upstream respiratory gas conduit with respect to the pressure of the external environment, as is characteristic of an exhalation process; and the second respiratory gas overpressure is an overpressure of the ambient pressure with respect to a lower pressure existing in the upstream respiratory gas conduit, as is characteristic, for example, for an inhalation process.

The statement that the valve subassembly permits an exhalation flow in an exhalation flow direction from the upstream respiratory gas conduit to the downstream respiratory gas conduit when the first respiratory gas overpressure exists, and prevents a flow in an opposite direction when the second predetermined respiratory gas overpressure exists, is not intended to exclude that in a context of pressure conditions deviating from the first and the second predetermined respiratory gas pressures, operating states of the valve subassembly can exist which are not recited initially in the Application. All that is critical is that the aforesaid operating states of the valve subassembly exist when the aforesaid respiratory gas overpressures exist.

The first and the second predetermined respiratory gas overpressure can each be a respiratory gas overpressure value range, so that different patients and patient types can be safely ventilated.

The terms "upstream" and "downstream" refer respectively, on the exhalation valve arrangement, to the exhalation flow direction that is unequivocally physically evident at that arrangement and is enabled when the predetermined first respiratory gas overpressure through the exhalation valve arrangement exists.

An exhalation valve arrangement of the species is known from WO 02/076544 A1.

A knowledge of the respiratory gas pressure existing upstream from the valve subassembly is useful in the interest of maximally exact functional control of the exhalation valve arrangement, in particular so that the PEEP brought about by the exhalation valve arrangement at the end of an exhalation process can be established as exactly as possible.

A flow sensor operating on the differential pressure principle, by way of which, because of its functional principle, information is also available regarding the pressure of the respiratory gas in the exhalation line, is often arranged in an exhalation line of a ventilation apparatus at its proximal end. Design-related possibilities for fault influences exist, however, between the respiratory gas pressure measurement point at the proximal end of the exhalation line and a measurement point located close to the valve subassembly but upstream therefrom, said influences resulting, for example, from the elasticity of an exhalation hose constituting the exhalation line to the exhalation valve arrangement, so that the pressure measurement at the proximal end of the exhalation line is less informative regarding the respiratory gas pressure that is actually present in the distal end region of the exhalation line in the upstream respiratory gas conduit upstream from the valve subassembly.

The object of the present invention is therefore to improve the exhalation valve arrangement recited initially in such a way that it makes possible a pressure detection in the expiratory respiratory gas upstream from the valve subassembly at a short distance therefrom. This is physically difficult as a rule because the upstream respiratory gas conduit of the exhalation valve arrangement is often, as a result of the design, not directly accessible, since as a rule it is radially externally encircled by an annular chamber immediately adjacently to the valve subassembly in an exhalation flow direction.

According to the present invention, the aforesaid object is achieved by an exhalation valve arrangement of the kind recited initially which comprises a bypass chamber which communicates in terms of flow mechanics with the upstream respiratory gas conduit and which extends, proceeding from the upstream respiratory gas conduit, into the region of the downstream respiratory gas conduit and is embodied there for attachment of a gas pressure sensor.

Because the downstream respiratory gas conduit usually opens toward the external environment of the exhalation valve arrangement or of the ventilation apparatus as a whole, in many cases the downstream respiratory gas conduit is more easily accessible than the upstream respiratory gas conduit. The bypass chamber extending in the region of the downstream respiratory gas conduit is therefore also easily accessible, as a rule even in a state already installed in a ventilation apparatus. The bypass chamber thus creates a measurement-capable access to the relatively well-concealed or well-incorporated upstream respiratory gas conduit, and makes the respiratory gas pressure present there detectable by a gas pressure sensor attached to the bypass chamber. The bypass chamber is specifically embodied for attachment of the gas pressure sensor.

The bypass chamber is preferably connected at a connecting region thereof, for example at its one longitudinal end, to the upstream respiratory gas conduit, and opens, for example, thereinto, and is embodied at an attachment region, for example at its opposite longitudinal end region, for attachment of the gas pressure sensor. In a simple but reliably functioning exemplifying embodiment, the bypass chamber can be implemented for attachment of a pressure sensor by the fact that a sensor attachment wall portion of a wall that delimits the bypass chamber comprises a sensor attachment opening that passes through the sensor attachment wall portion of the bypass chamber. The sensor attachment opening thus makes the interior of the bypass chamber accessible in principle from outside.

Advantageously, if the sensor attachment opening is closed off by a closure that can be selectably opened in order to attach a gas pressure sensor to the bypass chamber for measurement purposes, it can be left to the respective user, for example a caregiver or a supervising physician, whether detection of the respiratory gas pressure in the upstream respiratory gas conduit close to the valve subassembly is or is not in fact necessary or at least desirable. The reason is that there also exist simpler ventilation apparatuses in which no provision is made for detecting the pressure of the upstream respiratory gas, and which are not equipped for signal-related processing of such a pressure detection signal. The exhalation valve arrangement according to the present invention can also be used in such ventilation apparatuses by simply leaving the sensor attachment opening closed off by the closure.

Provision can be made in principle that in order to secure it against inadvertent opening and thus to prevent improper operation of the ventilation apparatus, the closure requires a relatively complex opening movement in order to open the sensor attachment opening and make it accessible for measurement-capable attachment of the gas pressure sensor. For example, the closure can be unscrewable from the sensor attachment opening; and to prevent inadvertent opening of the sensor attachment opening, preferably several rotations of the closure are required before it is released sufficiently from a closed position that it can be lifted away from the sensor attachment opening.

The time factor, however, is often very important when it comes to the use of life-sustaining medical devices, so that the exhalation valve arrangement needs to be usable on a ventilation apparatus as quickly as possible. Provision is therefore made, according to a preferred refinement of the present invention, that the closure encompasses a puncturable closure membrane that is constituted from a material that is softer compared with the material of the encircling sensor attachment wall portion. A softer material of this kind can be an elastomer, in particular a thermoplastic elastomer (TPE). Natural or silicone rubber has proven particularly successful in this context. A rim region of the closure which surrounds the closure membrane can then, for example, be adhesively bonded, or connected by vulcanization, by two-component injection molding, and/or by positive engagement, to a boundary region of the sensor attachment wall portion which surrounds the sensor attachment opening.

Alternatively or additionally, the closure can be connected to an additional component that, in the operationally ready state of the exhalation valve arrangement, interacts with the sensor attachment wall portion. An additional component of this kind can be a plug that, for example, closes off an opening that is unavoidably produced upon manufacture of the bypass chamber and is not the sensor attachment opening. The additional component can comprise a supplementary opening and can be provided in or on the exhalation valve arrangement in such a way that the sensor attachment opening and the supplementary opening at least partly overlap. The two openings preferably align with one another in order to furnish a sufficient attachment area for measurement-capable attachment of the gas pressure sensor. Here as well, the closure can encompass a closure membrane whose edge region that surrounds it, divergently from what was stated above, can be connected to a surrounding region of the additional component which surrounds the supplementary opening, once again utilizing one of the aforementioned effective principles. The additional component can be produced, for example, from polybutylene terephthalate or polyethylene terephthalate.

A component that constitutes the downstream respiratory gas conduit, in particular the conduit component recited below, can be constituted from polyester, in particular a co-polyester, or polycarbonate. Other materials are not excluded.

The advantage of an elastic membrane of this kind is not only that it can quickly be punctured and that the exhalation valve arrangement can thus quickly be made ready for use. A further advantage is that the flexible membrane constituted in this manner, similarly to a septum, can also fit sealingly around the component that is puncturing it, so that once the closure membrane has been punctured, an undesired gas flow between the bypass chamber and thus the upstream respiratory gas conduit on the one hand, and an external environment of the bypass chamber on the other hand, is ruled out. The closure membrane is preferably punctured by a tube that connects the bypass chamber in measurement-capable fashion to a pressure sensor.

A "measurement-capable connection" or "measurement-capable attachment" means, for purposes of the present Application, that the gas pressure sensor thereby attached by such connection or attachment is capable of detecting the pressure in the bypass chamber. Because the bypass chamber in turn communicates in flow-capable fashion with the upstream respiratory gas conduit, the gas pressure sensor that has thereby been attached can detect the pressure of the respiratory gas in the upstream respiratory gas conduit.

It is additionally advantageous in terms of the operating reliability of the exhalation valve arrangement if the risk of detachment of components and component portions can be eliminated. None of the component portions deriving from the exhalation valve arrangement can thus travel toward the patient and be inadvertently inhaled by him or her. Although this risk does not in fact exist in an exhalation line, the risk of a breakaway or detachment of membrane constituents upon puncturing of the closure membrane can be minimized or indeed completely excluded by the fact that the closure membrane comprises a normal region and a material weakening region, different from the normal region, in which the tearing strength of the membrane is decreased compared with the normal region.

It is thereby possible to ensure that the closure membrane tears in defined fashion when punctured. Defined tearing or defined destruction of the closure membrane not only ensures the sealing effect of the membrane after puncturing, since the membrane conformation of the closure membrane which exists after puncturing is known and predictable. The closure membrane equipped in this manner with a defined tearing point or a defined tearing region furthermore makes possible the use of attachment tubes having a comparatively large diameter, which has a positive influence on the accuracy of the measurement result of gas pressure sensors attached with such large attachment tubes or hoses. In the absence of the material weakening region, the tearing behavior of the membrane becomes less easily predictable as the size of the object puncturing the membrane increases.

The material weakening region can be constituted in simple fashion by the fact that the closure membrane has a thinner material thickness in the material weakening region than in the normal region.

The thinner material thickness can be brought about by way of incisions and/or indentations in the closure membrane. The incisions do not, of course, pass completely through the material of the closure membrane in a thickness direction, but are merely partial incisions over part of the thickness extent of the closure membrane.

To allow a defined, and also regular, tearing behavior of the closure membrane to be produced, such that an orientation of the object puncturing the closure membrane, for example an attachment hose or an attachment tube, is not important, the material weakening region is preferably embodied in patterned fashion in the closure membrane.

For example, the material weakening region can comprise a ring or several concentric rings, and/or the material weakening region can encompass at least two lines that intersect at the center of the membrane and divide the closure membrane respectively into membrane areas portions that are as identical as possible. In the preferred case of a circular closure membrane, these lines extend along diameters.

A simple and space-saving configuration of the exhalation valve arrangement, which is usable even though the bypass chamber is embodied in already-existing ventilation apparatuses, can be obtained by the fact that a portion of a wall that surrounds the downstream respiratory gas conduit forms the sensor attachment wall portion of the bypass chamber. The reason is that the bypass chamber can then proceed in the downstream respiratory gas conduit, so that the downstream respiratory gas conduit can have an outside diameter and an external conformation like those of an exhalation valve arrangement of identical design having no bypass chamber.

The exhalation valve arrangement can thus be manufactured with an already-known conformation and with already-known dimensions. This is also made possible by the fact that a large chamber volume is not required for the bypass chamber, and that the downstream respiratory gas conduit usually has in any case a large flow cross section that can be decreased by an amount equal to the cross section of the bypass chamber without appreciably interfering with the function of the downstream respiratory gas conduit and thus of the exhalation valve arrangement.

For weight reduction, the downstream respiratory gas conduit, having the bypass chamber located in it as already stated above, is embodied not with a double wall but with only a single wall. Because the bypass chamber has a smaller cross-sectional area when viewing a section plane orthogonal to the second conduit path, however, a portion of a partition that radially externally delimits the bypass chamber extends at a distance from a conduit wall that radially externally delimits the downstream respiratory gas conduit.

In order to reduce the risk that component portions might detach or separate in the exhalation valve arrangement and possibly travel as loose elements along unpredictable paths in the respiratory gas conduits, the exhalation valve arrangement is manufactured to the greatest extent possible in one piece. With reference to the bypass chamber that is important for the present invention, this preferably means that a partition in the downstream respiratory gas conduit, which separates the bypass chamber from the downstream respiratory gas conduit, is embodied in one piece with the conduit wall that surrounds the downstream respiratory gas conduit.

As a further guarantee of maximum component integrity, it is advantageous to reduce to a minimum any joining points in the exhalation valve arrangement. Provision can therefore be made, in accordance with a refinement, that a first exhalation tube that surrounds the upstream respiratory gas conduit, a second exhalation tube that surrounds the downstream respiratory gas conduit, and the partition that separates the bypass chamber from the downstream respiratory gas conduit are embodied in one piece as a conduit component.

A conduit component of this kind can be manufactured in one piece, for example, by injection molding, for example by using cores and sliders. Preferably, both the upstream and the downstream respiratory gas conduit respectively extend along a straight-line conduit axis constituting respectively the first and the second conduit path. The first and the second conduit axis preferably enclose an angle between them. Also preferably, the notionally prolonged conduit axes intersect one another. This not only makes possible a compact physical design for the conduit component, but also allows the valve body to be embodied as a membrane valve body that spans a longitudinal end of the upstream respiratory gas conduit, and makes it possible to embody the valve seat at the longitudinal end of the upstream respiratory gas conduit.

The upstream respiratory gas conduit can be radially externally encircled, at least at its longitudinal end that approaches the valve subassembly in an exhalation flow direction, by an annular chamber from which the downstream respiratory gas conduit branches off. The annular chamber is then located in terms of flow between the upstream and the downstream respiratory gas conduit in an exhalation flow direction. The membrane valve body can be secured on a wall that surrounds the annular chamber.

It is furthermore advantageous, for simple but nonetheless reliable visual monitoring of the exhalation valve arrangement, if the membrane valve body and the closure membrane are provided with mutually parallel membrane surfaces on the exhalation valve arrangement.

As a rule, the membrane valve body is incorporated into a ventilation apparatus in such a way that when the exhalation valve arrangement is in the operationally ready position in the ventilation apparatus, the membrane valve body is preloaded by gravity toward the valve seat, i.e. toward a closed position. A device of the ventilation apparatus which is embodied to impinge upon the membrane valve body with a predetermined or adjustable force acting in a closing direction is furthermore often present on that side of the membrane valve body which faces away from the respiratory gas conduits. This device can be a mechanical device, for example a plunger and the like; or it can be a pneumatic device, for example a gas container which can be impinged upon by a pressure and of which the membrane valve body forms part of the delimiting surface.

The exhalation valve arrangement is therefore often introduced into the housing of a ventilation apparatus, and into its operationally ready position. oppositely to the direction of gravity.

Advantageously, an attachment tube for attaching a gas pressure sensor can already be fixedly arranged in the housing of the ventilation apparatus. In an advantageously simple manner, the gas pressure sensor can already be attached to the upstream respiratory gas conduit, concurrently with installation of the exhalation valve arrangement into the ventilation apparatus, if the closure membrane is arranged orthogonally to the direction of gravity when the exhalation valve arrangement is arranged in operationally ready fashion, such that its outer side facing away from the bypass chamber faces oppositely to the direction of gravity. Upon introduction of the exhalation valve arrangement into a housing of the ventilation apparatus, the closure membrane can thereby be punctured by the housing-mounted attachment tube in the course of the introduction movement.

The present invention also relates to a ventilation apparatus for artificial ventilation of patients, having a respiratory gas supply apparatus from which an inhalation line leads to a patient ventilation interface, from which an exhalation line leads in turn to a respiratory gas sink, for example the ambient atmosphere. Provision is made according to the present invention, in order to achieve the effects and advantages recited above, that an exhalation valve arrangement as described and refined above is provided in the exhalation line. In this context, the upstream respiratory gas conduit is connected by a portion of the exhalation line to the patient ventilation interface in order to transfer expiratory respiratory gas from the patient ventilation interface.

The embodiments of a ventilation apparatus which are presented above in order to explain the exhalation valve arrangement according to the present invention are refinements according to the present invention of the ventilation apparatus recited in the preceding paragraph.

The present invention will be explained in further detail below with reference to the appended drawings, in which.

Figure 1:
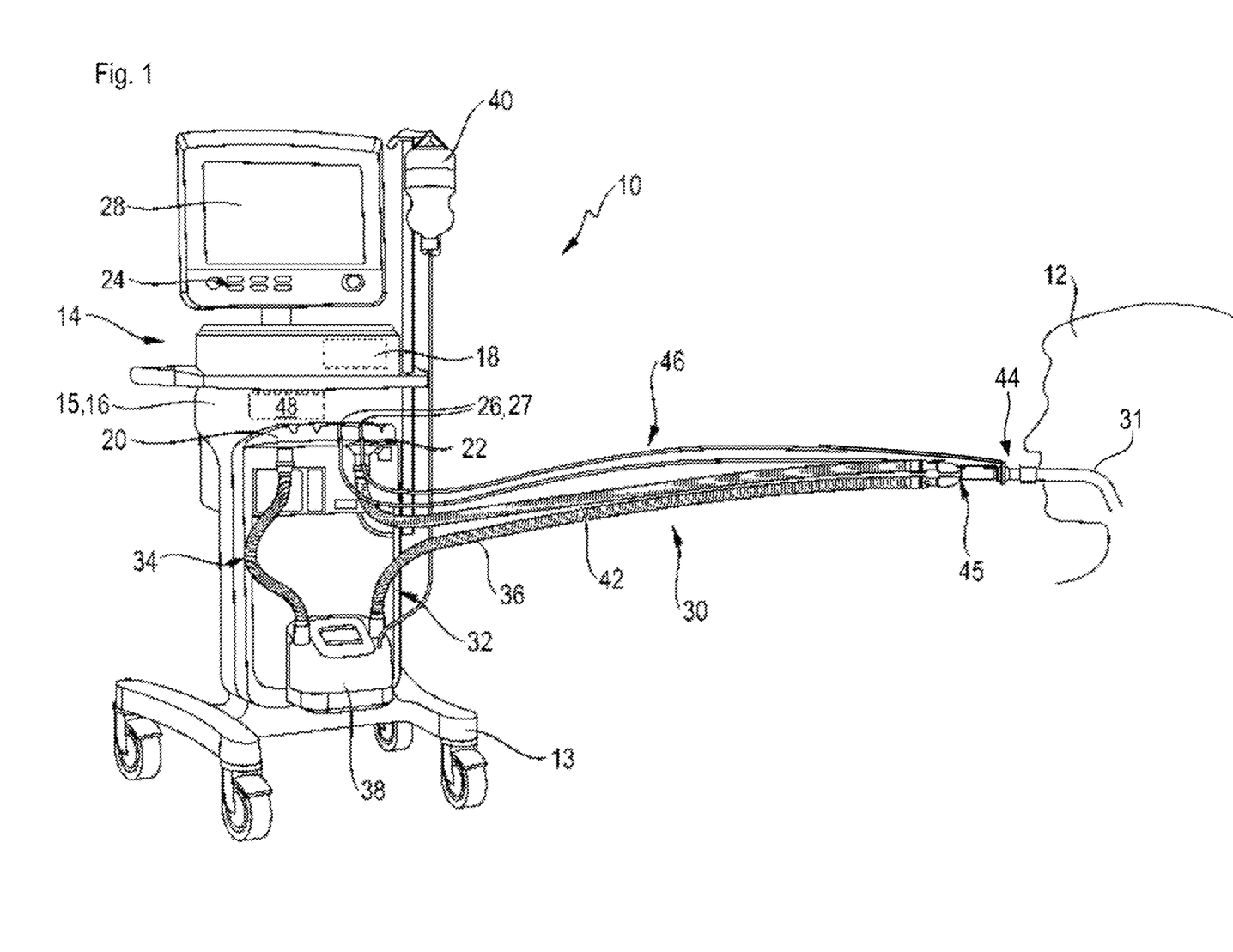
FIG. 1 depicts a ventilation apparatus having an embodiment according to the present invention of a exhalation valve arrangement.

In order to explain the exhalation valve arrangement according to the present invention, firstly a ventilation apparatus that uses the exhalation valve arrangement will be explained with reference to FIG. 1:

In FIG. 1, a ventilation apparatus is labeled in general with the number 10. In the example depicted, ventilation apparatus 10 serves for artificial ventilation of a human patient 12. Ventilation apparatus 10, constituting a mobile ventilation apparatus 10, can be received on a rollable frame 13.

Ventilation apparatus 10 comprises a housing 14 in which a pressure modification arrangement 16 and a control device 18 (not visible from outside because the housing material is opaque) can be received.

Pressure modification arrangement 16 is constructed in a manner known per se and comprises a respiratory gas supply apparatus 15 in the form of a pump 15, a compressor, or a fan, which are respectively controllable in modifiable-load fashion and therefore serve not only to introduce ventilation gas into the ventilation apparatus but also to modify the pressure of the ventilation gas that is introduced. Respiratory gas supply apparatus 15 can also, alternatively, be constituted by a pressure vessel that is connectable to housing 14 of ventilation apparatus 10. Pressure modification apparatus 16 can comprise respiratory gas supply apparatus 15 and, if applicable, additionally (or, in the case of a pressurized gas reservoir constituting a respiratory gas supply apparatus, alternatively) a reducing valve and the like. Ventilation apparatus 10 furthermore comprises, in a manner known per se, an inhalation valve arrangement 20 and an exhalation valve arrangement 22 that, in FIG. 1, are concealed by housing 14 of ventilation apparatus 10. Exhalation valve arrangement 22 is an exhalation valve arrangement in accordance with the present invention.

Control device 18 is usually implemented as a computer or microprocessor. It encompasses a data storage device (not depicted in FIG. 1) so that data necessary for the operation of ventilation apparatus 10 can be stored and retrieved as necessary. In a network operating mode, the storage device can also be located outside housing 14 and can be connected to control device 18 by a data transfer connection. The data transfer connection can be constituted by a cable link or a radio link. In order to prevent disruptions in the data transfer connection from being able to affect the operation of ventilation apparatus 10, however, the storage device is preferably integrated into control device 18 or at least received in the same housing 14 with it.

Ventilation apparatus 10 has a data input 24, which is represented by a keyboard in the example depicted in FIG.

1, for the input of data into ventilation apparatus 10 or more precisely into control device 18. Alternatively or in addition to the keyboard that is depicted, control device 18 can obtain data via various data inputs 26, for example via a network lead, a radio link, or via sensor terminals that are discussed in detail below.

Ventilation apparatus 10 can comprise an output device 28, in the example depicted a screen, for outputting data to the therapist providing treatment.

For artificial ventilation, patient 12 is connected to ventilation apparatus 10, more precisely to pressure modification arrangement 16 in housing 14, via a ventilation line arrangement 30. Patient 12 is intubated for that purpose with an endotracheal tube 31.

Ventilation line arrangement 30, through which fresh ventilation gas can be directed from respiratory gas supply apparatus 15 and pressure modification arrangement 16 into the lungs of patient 12, comprises an inhalation hose 32 outside housing 14. Inhalation hose 32 can be interrupted, and can comprise a first partial inhalation hose 34 and a second partial inhalation hose 36, between which a conditioning device 38 can be provided for controlled humidification and optionally also temperature control of the fresh ventilation gas delivered to patient 12. Conditioning device 38 can be connected to an external liquid reservoir 40 by way of which water for humidification, or also a medication, for example to inhibit inflammation or to dilate the airways, can be delivered to the ventilation gas. When the present ventilation apparatus 10 is used as an anesthesia ventilation apparatus, volatile anesthetics can thereby be delivered in controlled fashion to patient 12 via ventilation apparatus 10. Conditioning device 38 ensures that the fresh respiratory gas is conveyed to patient 12 with a predetermined moisture content, optionally with addition of a medication aerosol, and at a predetermined temperature.

Ventilation line arrangement 30 comprises, in addition to inhalation valve arrangement 20 already mentioned, exhalation valve arrangement 22 and furthermore an exhalation hose 42 through which metabolized respiratory gas from the lungs of patient 12 is exhausted into the atmosphere.

Inhalation hose 32 is coupled to inhalation valve arrangement 20, and exhalation hose 42 to exhalation valve arrangement 22. Any actuation control of valve arrangements 20 and 22, beyond automatic control resulting from ventilation, is also effected via control device 18.

During a ventilation cycle, firstly exhalation valve arrangement 22 is closed and inhalation valve arrangement 20 is opened for the duration of the inhalation phase, so that fresh respiratory gas can be directed from housing 14 to patient 12 only via inhalation hose 32. A flow of fresh respiratory gas is produced by a controlled elevation of the pressure of the respiratory gas by pressure modification arrangement 16. As a result of the pressure elevation, the fresh respiratory gas flows into the lungs of patient 12, where it expands the body region in the vicinity of the lungs, i.e. in particular the thorax, against the individual elasticity of the body parts near the lungs. The gas pressure in the interior of the lungs of patient 12 also rises as a result.

At the end of the inhalation phase, inhalation valve arrangement 20 is closed and exhalation valve arrangement 22 is opened. The exhalation phase begins. Because the gas pressure of the respiratory gas present in the lungs of patient 12 has been elevated until the end of the inhalation phase, said gas flows into the atmosphere through exhalation valve arrangement 22 after the latter is opened, while the gas pressure in the lungs of patient 12 decreases as the flow continues. Once the gas pressure in lungs of patient 12 reaches a positive end expiratory pressure (PEEP) that is set on ventilation apparatus 10, i.e. a pressure slightly higher than atmospheric pressure, the exhalation phase is terminated and is followed by a further ventilation cycle.

During the inhalation phase, the so-called ventilation tidal volume, i.e. the volume of respiratory gas for each breath, is delivered to patient 12. The ventilation tidal volume multiplied by the number of ventilation cycles per minute, i.e. multiplied by the ventilation frequency, equals the volume of artificial ventilation per minute being performed in the present case.

Ventilation apparatus 10, in particular control device 18, is preferably embodied to repeatedly update or ascertain, during ventilation operation, ventilation operating parameters that characterize the ventilation operation of ventilation apparatus 10, in order to ensure that ventilation operation is coordinated as optimally as possible, at every point in time, with patient 12 who is respectively to be ventilated. Particularly advantageously, the determination of one or several ventilation operation parameters is made at the ventilation frequency, so that ventilation operating parameters that are current, and thus optimally adapted to patient 12, can be furnished for each ventilation cycle.

Ventilation apparatus 10 is data-transferringly connected for this purpose to one or several sensors that monitor the status of the patient and/or monitor operation of the ventilation apparatus.

One of these sensors is a proximal flow sensor 44 that is arranged at that end of a Y-connector piece 45 which is located closer to patient 12, and detects the ventilation gas flow existing at that point in ventilation line arrangement 30. Flow sensor 44 can be coupled by means of a sensor lead arrangement 46 to data inputs 26 of control device 18. Sensor lead arrangement 46 can, but does not need to, encompass electrical signal transfer leads. It can likewise comprise hose lines that transfer the gas pressure existing in a flow direction on either side of flow sensor 44 to data inputs 26, where that pressure is quantified by pressure sensors 27. Flow sensor 44 is preferably a flow sensor operating on the differential pressure principle, but can also be a flow sensor operating in accordance with a different physical operating principle.

A further flow sensor 48, which is referred to as a "distal" flow sensor 48 because of its greater distance from patient 12 compared with the proximal flow sensor 44, is provided in housing 14.

Figure 2:
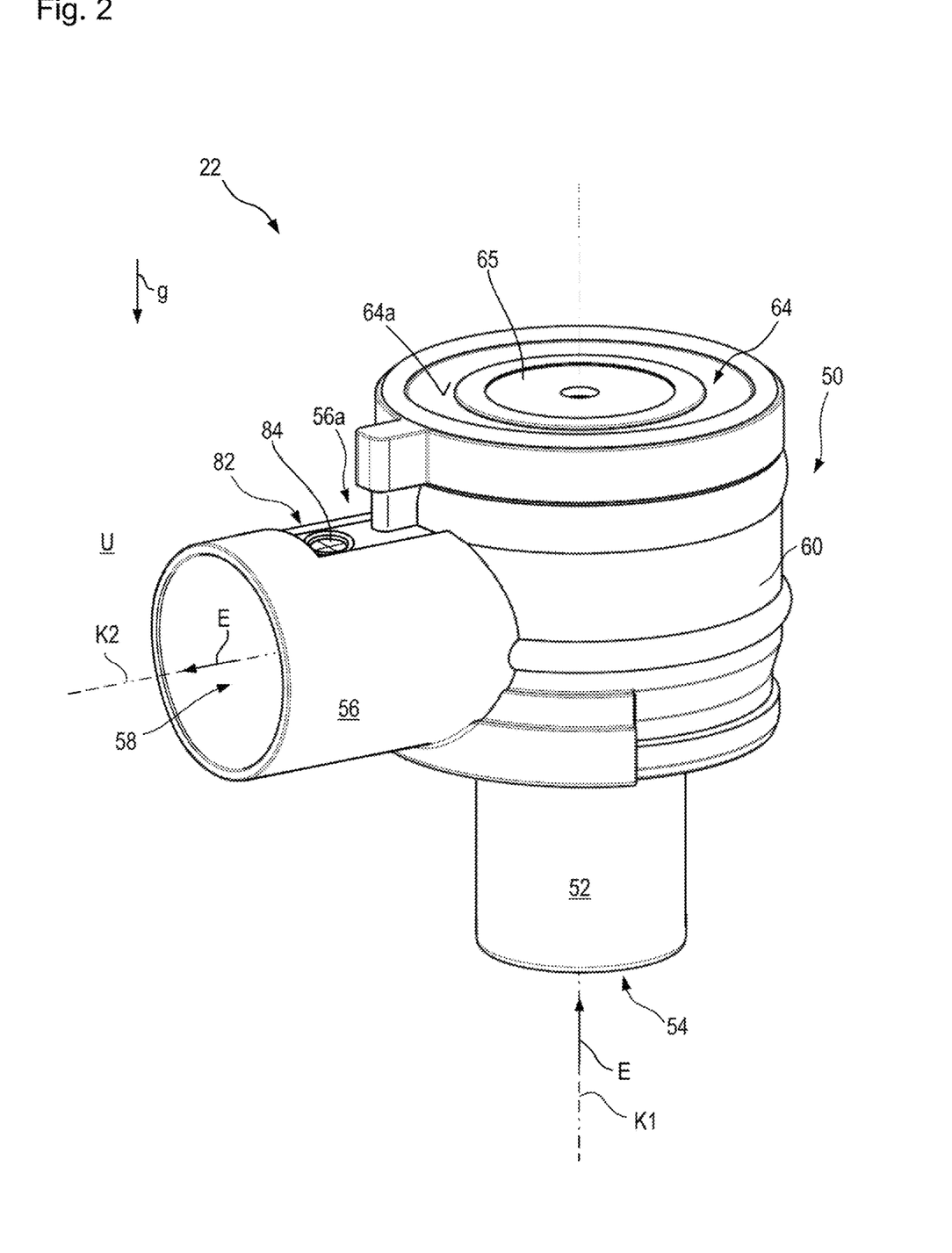
FIG. 2 is a perspective view of a first embodiment according to the present invention of an exhalation valve arrangement of the present Application.
Figure 4:
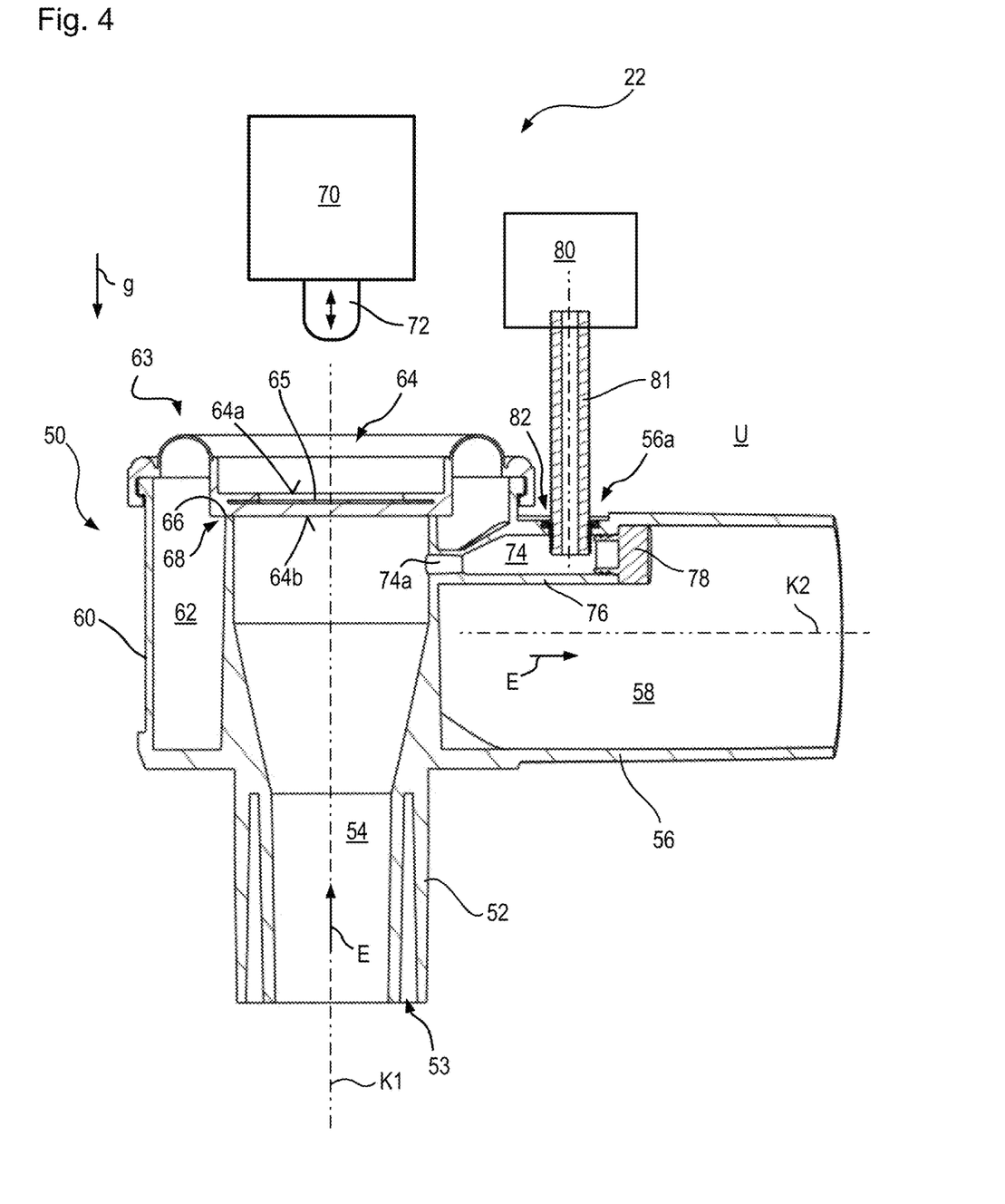
FIG. 4 is a longitudinal section view through the exhalation valve arrangement of FIG. 2, in a section plane that contains the first and the second conduit path.

FIG. 2 is a perspective depiction of exhalation valve arrangement 22, removed from housing 14 of ventilation apparatus 10. FIG. 4 is a schematic depiction of exhalation valve arrangement 22 in longitudinal section.

Exhalation valve arrangement 22 will be explained below in further detail with reference to FIGS. 2 and 4.

Exhalation valve arrangement 22 encompasses a conduit component 50, manufactured substantially in one piece by injection molding, having an upstream exhalation tube 52 that radially outwardly delimits an upstream respiratory gas conduit 54, and having a downstream exhalation tube 56 that surrounds a downstream respiratory gas conduit 58. Upstream respiratory gas conduit 54 extends along first conduit path K1 configured as a straight-line conduit axis; downstream respiratory gas conduit 58 extends along the second conduit path that is likewise embodied as a straight-line conduit path K2.

Expiratory respiratory gas is capable of flowing through exhalation valve arrangement 22 in exhalation flow direction E.

A downstream end portion of upstream exhalation tube 52 is radially externally encircled by an annular chamber tube 60 that radially externally delimits an annular chamber 62. Annular chamber 62 is radially internally delimited by upstream exhalation tube 52.

Exhalation valve arrangement 22 comprises, in the region of the downstream end of upstream exhalation tube 52, a valve subassembly (see FIG. 4) having a membrane valve body 64 and further having a valve seat 66.

Membrane valve body 64 is mounted at that longitudinal end of annular chamber tube 60 which is located closer to the downstream longitudinal end of upstream exhalation tube 52 and comprises, on its side 64b facing toward upstream exhalation tube 52, a valve seat surface with which membrane valve body 64 can rest on valve seat 66 that is embodied at the downstream longitudinal end of upstream exhalation tube 52.

When exhalation valve arrangement 22 is in the operationally ready installation position, first conduit path K1 extends parallel to direction of gravity g, so that membrane valve body 64 is preloaded by gravity into the closed position shown in FIG. 4, in which membrane valve body 64 rests on valve seat 66 and separates upstream respiratory gas conduit 54 in terms of flow from downstream respiratory gas conduit 58.

Downstream respiratory gas conduit 58 opens into external environment U, which constitutes a respiratory gas sink of ventilation apparatus 10 and of exhalation valve arrangement 22. Ambient pressure is thereby impressed upon the expiratory respiratory gas from the downstream longitudinal end of downstream exhalation tube 56.

When an overpressure with respect to ambient pressure exists in upstream respiratory gas conduit 54 (as is typical for an exhalation process), and ambient pressure furthermore also acts on that side 64a of membrane valve body 64 which faces away from valve seat 66, membrane valve body 64 becomes lifted off from valve seat 66 substantially along first conduit path K1, so that an annular gap 68, whose gap height in FIG. 4 is still equal to zero, is formed between valve seat 66 and that side 64b of membrane valve body 64 which faces toward valve seat 66.

When valve subassembly 63 is open, expiratory respiratory gas therefore flows, driven by the relative overpressure in upstream respiratory gas conduit 54, through valve gap 68 into annular chamber 62 and from there into downstream respiratory gas conduit 58 and lastly into external environment U.

For better orientation, be it noted that upstream exhalation tube 52 comprises, at its upstream longitudinal end region opposite from valve seat 66, a connecting configuration 53 with which upstream exhalation tube 52, and therefore exhalation valve arrangement 22, are connectable to exhalation hose 42 of FIG. 1.

The relative overpressure existing in upstream respiratory gas conduit 54 with respect to the gas pressure in downstream respiratory gas conduit 58 decreases as the duration of the exhalation process increases. It is important in this context to maintain a positive end expiratory pressure (PEEP) in order to apply a positive counter-pressure to the patient's lungs until the end of the exhalation process and thereby prevent the artificially ventilated patient's lungs from collapsing.

The PEEP is adjusted by adjusting the gap height of valve gap 68. Exhalation valve arrangement 22 encompasses for that purpose an actuator 70 (depicted only in FIG. 4), for example an electromagnetic actuator 70, from which a plunger 72 can be extended and retracted again by control device 18 of ventilation apparatus 10.

Plunger 72 can be brought, with its longitudinal end which is remote from the remainder of actuator 70 and which is toward the front in the context of an extension movement, into abutting engagement with a rigid plate 65 in membrane valve body 64, so that membrane valve body 64 is movable in defined fashion toward valve seat 66 by actuator 70. No provision is made, however, for a lifting of membrane valve body 64 off from valve seat 66 by plunger 72 or by actuator 70, since only compressive forces, but no pulling forces, can be transferred by the abutting engagement between plunger 72 and rigid plate 65.

A knowledge of the respiratory gas pressure existing, as close as possible to valve seat 66, in upstream respiratory gas conduit 54 is useful for an accurate adjustment of the positive end expiratory pressure by actuator 70.

Exhalation valve arrangement 22 according to the present invention comprises for that purpose a bypass chamber 74 (see FIG. 4) inside downstream exhalation tube 56. This bypass chamber 74 communicates in flow-capable fashion at its longitudinal end 74a with upstream respiratory gas conduit 54. The result is that the gas pressure present in bypass chamber 74 is the same as at the downstream end of upstream respiratory gas conduit 54.

A partition 76 that separates the bypass chamber from downstream respiratory gas conduit 58 is preferably embodied in one piece with exhalation tubes 52 and 56, and with annular chamber tube 60. This yields a compact arrangement from which components or component portions cannot become detached.

Because partition 76 is embodied in one piece with conduit component 50, an opening of bypass chamber 74 which is occupied by a slider in the context of manufacture by injection molding must be closed off by a plug 78 on the completed exhalation valve arrangement 22. Plug 78 can be connected to the remainder of conduit component 50 by frictional engagement or by adhesive bonding or by welding.

A sensor attachment wall portion 56a of downstream exhalation tube 56 which faces preferably oppositely to the direction of gravity g when exhalation valve arrangement 22 is in the installed state, said portion surrounding both downstream respiratory gas conduit 58 and bypass chamber 74 at the location where sensor attachment wall portion 56a is embodied, is configured for measurement-capable attachment of a gas pressure sensor 80 (see FIG. 4).

Figure 3:
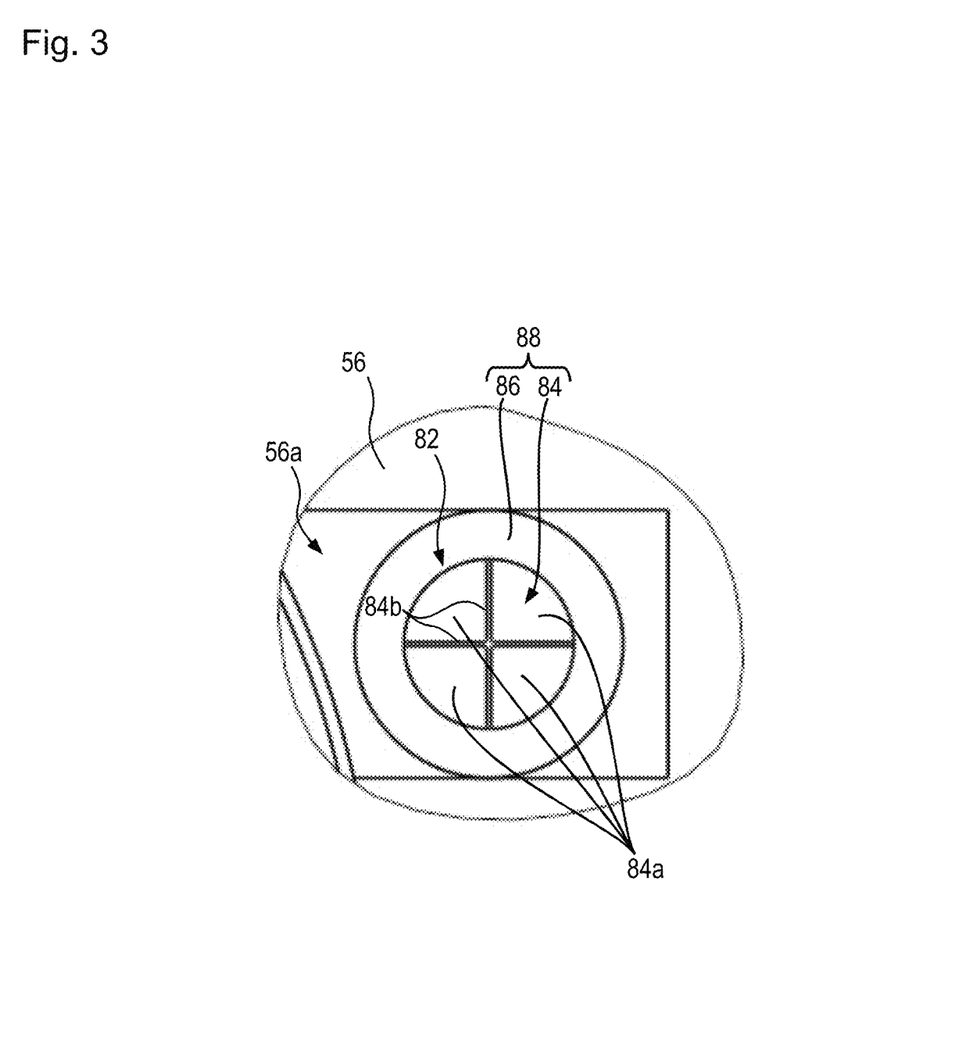
FIG. 3 is a top view of a closure of a sensor attachment opening in the form of a closure membrane, on the first embodiment of the exhalation valve arrangement.
Figure 5:
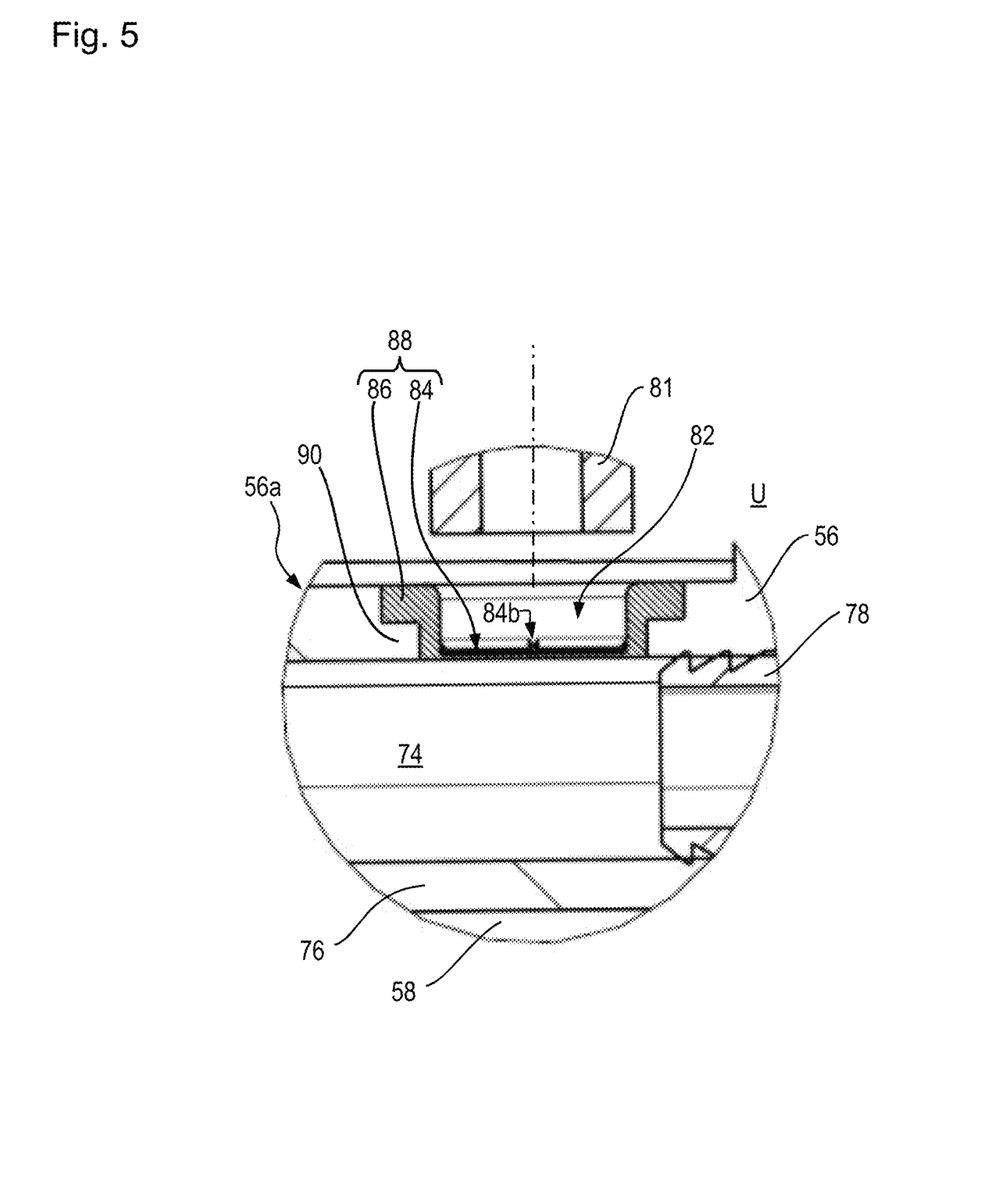
FIG. 5 is a detail view of the longitudinal section of FIG. 4, with an intact closure membrane and with an attachment tube arranged at a distance therefrom outside the bypass chamber.
Figure 6:
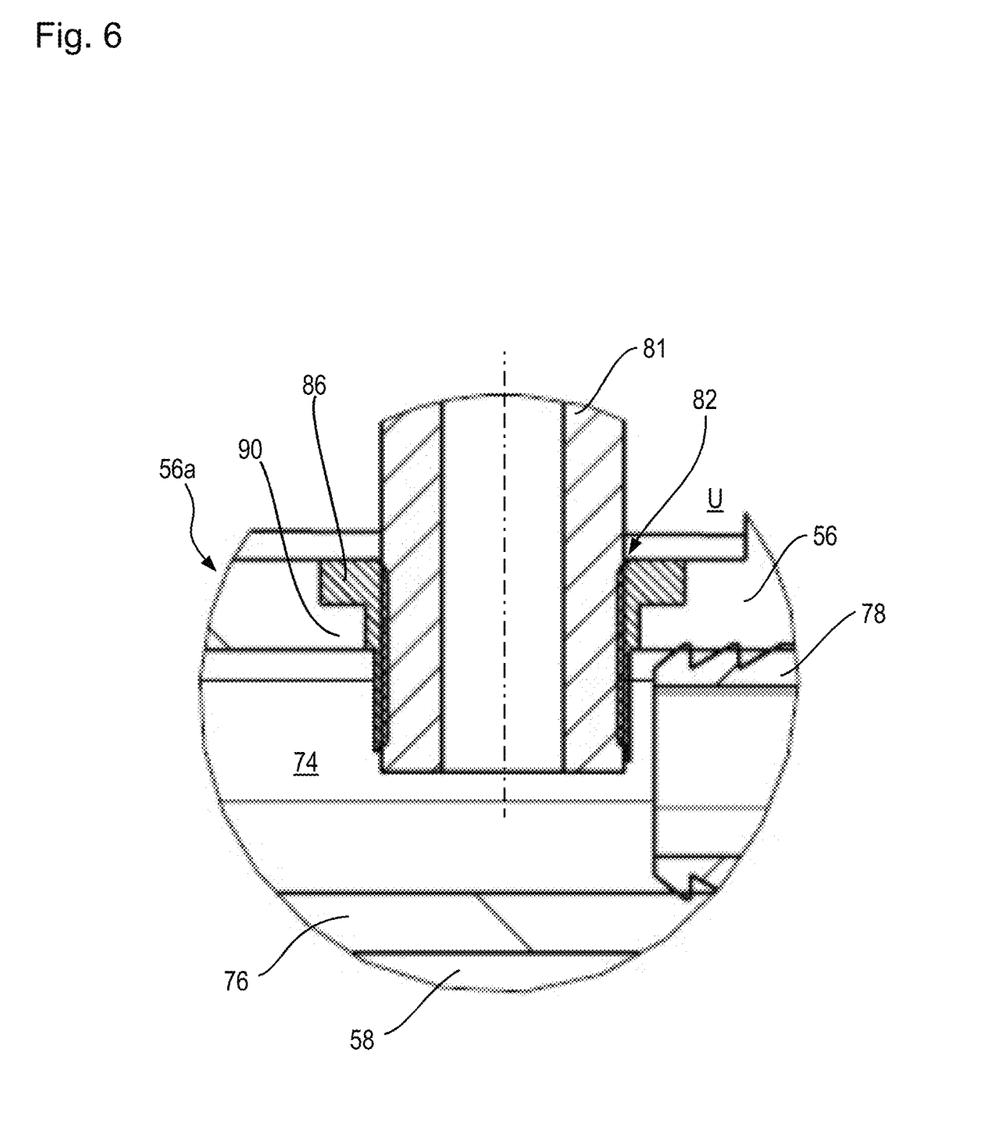
FIG. 6 is the view of FIG. 5 with the attachment tube passing through the sensor attachment opening after the closure membrane has been punctured.

In FIGS. 4 and 6, gas pressure sensor 80 is depicted as being attached in measurement-capable fashion to the bypass chamber and thus to upstream respiratory gas conduit 54; in FIGS. 2, 3, and 5, exhalation valve arrangement 22 is depicted as being merely embodied for attachment of a gas pressure sensor, but without implementation of that attachment.

The result is that exhalation valve arrangement 22 can be operated both with a gas pressure sensor 80 attached in measurement-capable fashion via bypass chamber 74 to upstream respiratory gas conduit 54, and without such attachment.

Embodied in sensor attachment wall portion 56a, which is preferably embodied, for simpler processing, with a flat outer surface on its side that faces radially away from downstream respiratory gas conduit 58 and from bypass chamber 74, is a sensor attachment opening 82 that passes completely through sensor attachment wall portion 56a in a thickness direction of downstream exhalation tube 56. This sensor attachment opening 82 is initially closed off by a closure membrane 84 (see FIGS. 2, 3, and 5). Closure membrane 84 can easily be punctured, however, and bypass chamber 74 can thereby be made accessible from external environment U. FIGS. 4 and 6, for example, depict the manner in which closure membrane 84 that originally spanned sensor attachment opening 82 has been punctured by an attachment tube 81 that connects the internal region of bypass chamber 74 in measurement-capable fashion to gas pressure sensor 80.

As is evident from FIG. 3, closure membrane 84 can be surrounded by a rim region 86 that is contiguous with closure membrane 84 and is nondetachably connected, for example by adhesive bonding, to sensor attachment wall portion 56a. Closure membrane 84 and rim region 86 then constitute a closure 88 that closes off sensor attachment opening 82.

As is evident in particular from FIG. 5, rim region 86 of closure 88 is adhesively bonded to a boundary region 90, encircling sensor attachment opening 82, of sensor attachment wall portion 56a.

In the unopened state, membrane 84 comprises a normal region 84a and a material weakening region 84b that has a thinner membrane wall thickness than normal region 84a.

As depicted by way of example in FIG. 3, material weakening region 84b encompasses two diameter lines which intersect one another at right angles and along which membrane 84 has a thinner wall thickness than in the regions on either side of those lines. Normal region 84a is thereby divided into four sub-regions of equal size, each of which respectively occupies one quadrant of membrane 84 that is circular in the example. Each diameter line of material weakening region 84b divides membrane 84 into two surface regions of approximately equal size.

Thanks to the configuration of material weakening region 84b, upon puncturing by attachment tube 81 as shown in FIGS. 4 to 6, membrane 84 tears along the lines of material weakening region 84b which form the defined tearing points, so that membrane 84 opens in a predetermined manner when punctured by an attachment tube 81.

As shown in FIG. 6, both rim region 86 of closure 88 and the membrane residues can radially externally seal the attachment opening tube 81 at the location of the punctured sensor attachment opening 82, and thus prevent undesired gas flows between the interior of bypass chamber 74 and external environment U, and thus a distortion of the gas pressure ascertained by gas pressure sensor 80 in upstream respiratory gas conduit 54.

Figure 7:
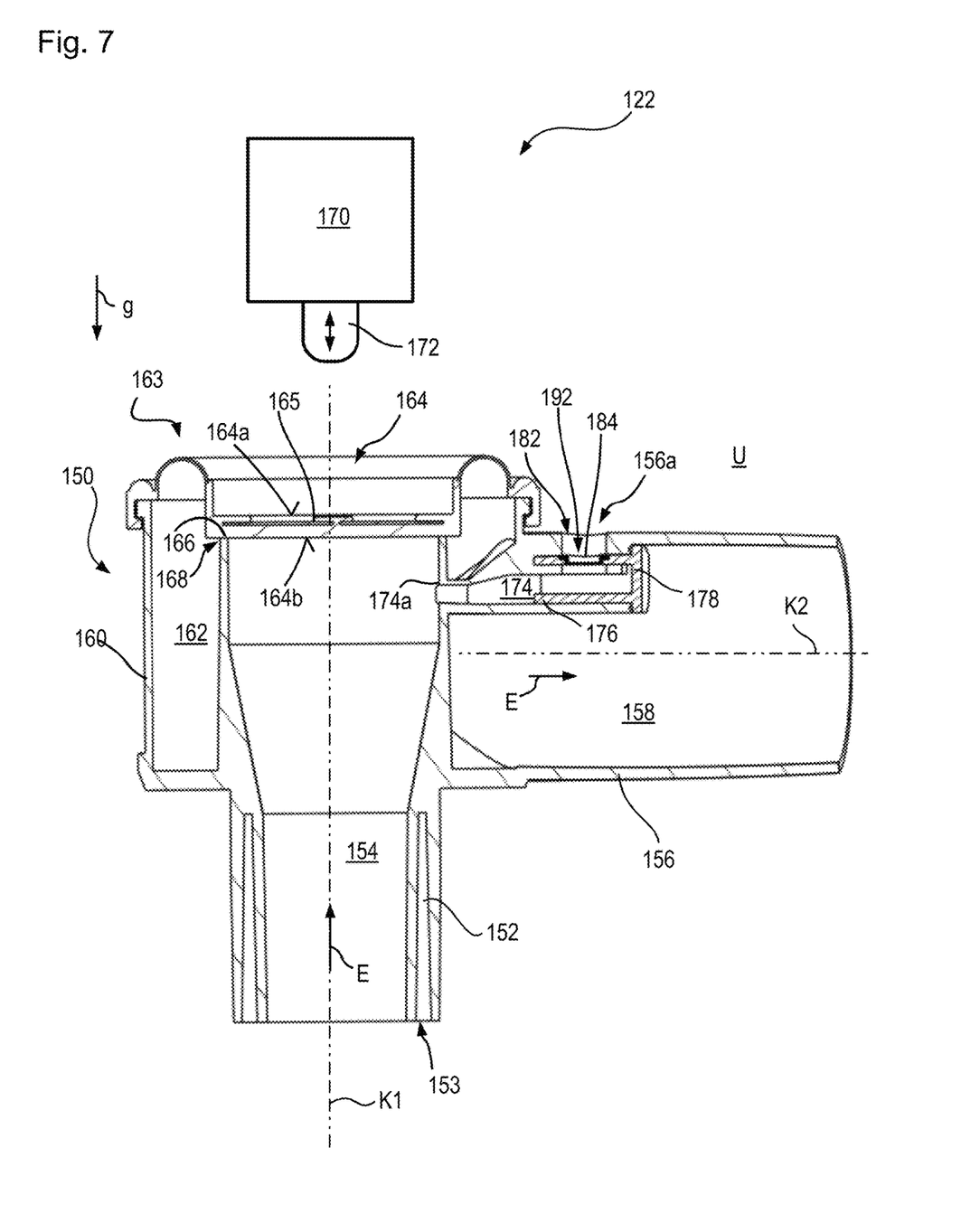
FIG. 7 is a longitudinal section view, corresponding to the view of FIG. 2, through a second embodiment of an exhalation valve arrangement of the present Application.

FIG. 7, using the same perspective and the same section plane location as in FIG. 2, shows a second embodiment of an exhalation valve arrangement according to the present invention. Components and component portions that are identical and functionally identical to those in the first embodiment are labeled in the second embodiment with the same reference characters as in the first embodiment of FIGS. 2 to 6, but incremented by 100.

The second embodiment will be described below only insofar as it differs from the first embodiment, to the description of which reference is otherwise made for an explanation of the second embodiment of FIGS. 7 and 8 as well.

Figure 8:
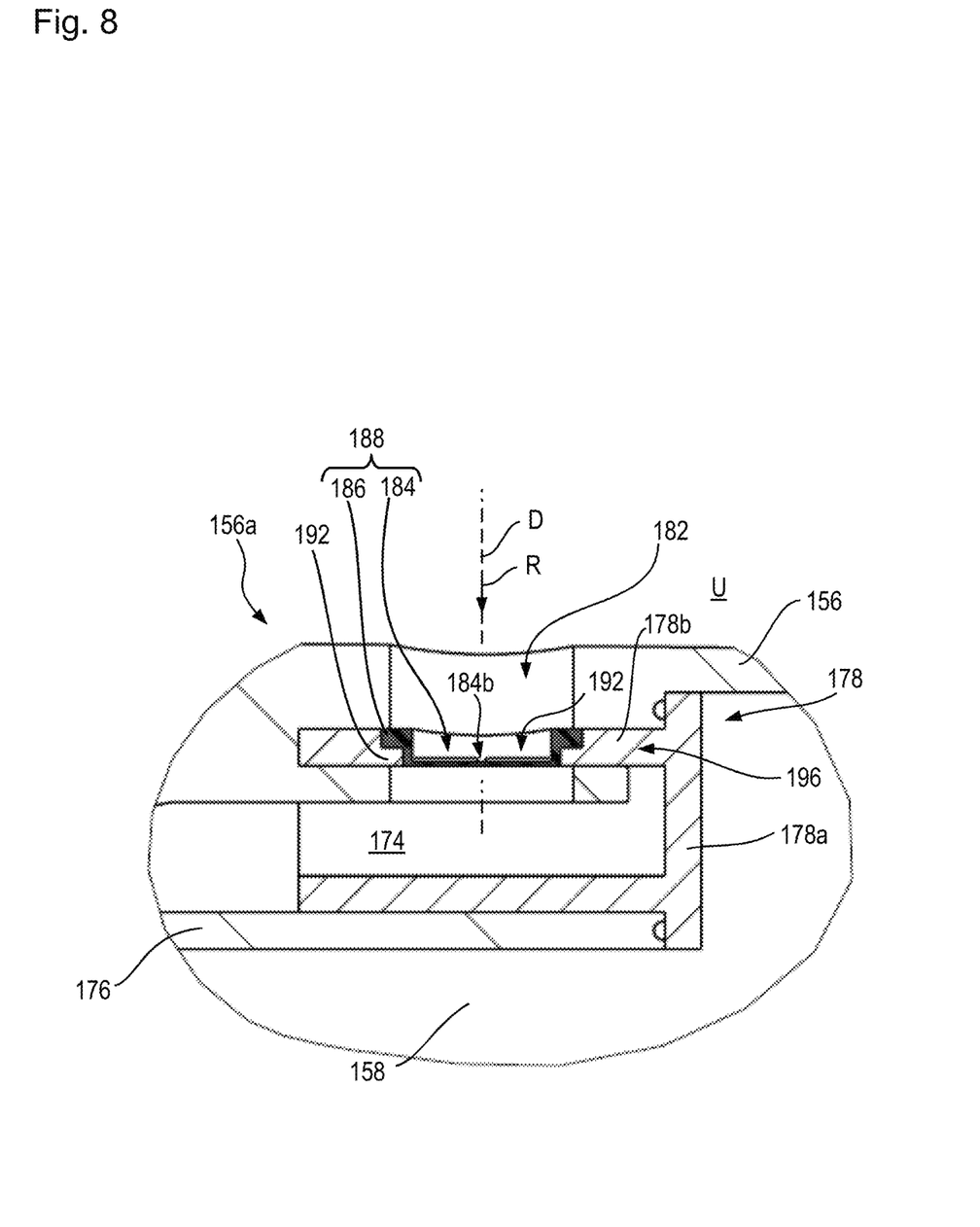
FIG. 8 is a detail view of the longitudinal section of FIG. 7, with an intact closure membrane.

In the second embodiment depicted in FIGS. 7 and 8, closure 188 (see FIG. 8) is provided at plug 178 as an additional component interacting with sensor attachment wall portion 156a. Plug 178 has, at a fastening limb, for example a continuously circumferential fastening sleeve 178b, which protrudes from a plug head 178a, a supplementary opening 192 that overlaps with sensor attachment opening 182, preferably with coaxial opening axes that pass centrally through the respective openings 182 and 192. In the present second exemplifying embodiment, rim region 186 that surrounds closure membrane 184 is connected, for example by two-component injection molding, to a surrounding region 184 that surrounds supplementary opening 192.

When exhalation valve arrangement 122 is in the operationally ready state, the fastening limb, in particular in the form of the continuously circumferential fastening sleeve 178b, surrounds a portion of the internal volume of bypass chamber 174.

That portion of plug 178 which comprises supplementary opening 192 can be received in sensor attachment wall portion 156a in a receiving configuration 196 that delimits that plug portion on both sides along a penetration axis D of supplementary opening 192. The plug portion that comprises supplementary opening 192 can also, however, as in the first exemplifying embodiment, merely be received radially externally by material of downstream exhalation tube 156, or between partition 176 and sensor attachment wall portion 156a.

Sensor attachment opening 182 is preferably no smaller than supplementary opening 192, and also preferably has the same conformation. Sensor attachment opening 182 can be slightly larger than, or the same size as, supplementary opening 192, especially if material of sensor attachment wall portion 156a is still present behind (in penetration direction R along penetration axis D) the plug portion that comprises supplementary opening 192. At least that part of sensor attachment opening 182 which is located behind supplementary opening 192 in penetration direction R can be larger than supplementary opening 192, in order to furnish, for the membrane residues that project from rim region 186 in penetration direction R after closure membrane 184 has been punctured, a receiving space between sensor attachment wall portion 156a and an attachment tube that passes through sensor attachment opening 182 and supplementary opening 192.

The invention claimed is:

1. An exhalation valve arrangement for an exhalation line of a ventilation apparatus for artificial ventilation of patients, the exhalation valve arrangement being flow-capable in an exhalation flow direction and comprising:
    an upstream respiratory gas conduit that extends along a first conduit path and is connected or connectable to a portion coming from the patient, of the exhalation line;
    a downstream respiratory gas conduit that extends along a second conduit path and is connected or connectable to a respiratory gas sink
    a valve subassembly which comprises a valve body and a valve seat and which is provided between the upstream and the downstream respiratory gas conduit in such a way that, in the context of a predetermined first respiratory gas overpressure in the upstream respiratory gas conduit relative to the downstream respiratory gas conduit, it permits an expiratory respiratory gas flow from the upstream respiratory gas conduit into the downstream respiratory gas conduit; and in the context of a predetermined second respiratory gas overpressure in the downstream respiratory gas conduit relative to the upstream respiratory gas conduit, it blocks a gas flow from the downstream respiratory gas conduit into the upstream respiratory gas conduit,
    wherein the exhalation valve arrangement comprises a bypass chamber which communicates in terms of flow mechanics with the upstream respiratory gas conduit and which extends, proceeding from the upstream respiratory gas conduit, into the region of the downstream respiratory gas conduit and is embodied there for attachment of a gas pressure sensor.

2. The exhalation valve arrangement according to claim 1, wherein a sensor attachment wall portion of a wall that delimits the bypass chamber comprises a sensor attachment opening that passes through the sensor attachment wall portion of the bypass chamber, the sensor attachment opening being closed off by an openable closure.

3. The exhalation valve arrangement according to claim 2, wherein the closure encompasses a puncturable closure membrane that is constituted from a material that is softer compared with the material of the encircling sensor attachment wall portion.

4. The exhalation valve arrangement according to claim 3, wherein the closure membrane is constituted from an elastomer.

5. The exhalation valve arrangement according to claim 4, wherein the closure membrane comprises a normal region and a material weakening region, different from the normal region, in which the tearing strength of the closure membrane is decreased compared with the normal region.

6. The exhalation valve arrangement according to claim 5, wherein the closure membrane has a thinner material thickness in the material weakening region than in the normal region.

7. The exhalation valve arrangement according to claim 6, wherein the material weakening region is embodied in patterned fashion in the closure membrane.

8. The exhalation valve arrangement according to claim 5, wherein the material weakening region is embodied in patterned fashion in the closure membrane.

9. The exhalation valve arrangement according to claim 3, wherein the closure membrane comprises a normal region and a material weakening region, different from the normal region, in which the tearing strength of the closure membrane is decreased compared with the normal region.

10. The exhalation valve arrangement according to claim 9, wherein the closure membrane has a thinner material thickness in the material weakening region than in the normal region.

11. The exhalation valve arrangement according to claim 10, wherein the material weakening region is embodied in patterned fashion in the closure membrane.

12. The exhalation valve arrangement according to claim 9, wherein the material weakening region is embodied in patterned fashion in the closure membrane.

13. The exhalation valve arrangement according to claim 3, wherein the closure membrane is constituted from natural or silicone rubber.

14. The exhalation valve arrangement according to claim 1, wherein a portion of a wall that surrounds the downstream respiratory gas conduit forms the sensor attachment wall portion of the bypass chamber.

15. The exhalation valve arrangement according to claim 1, wherein the bypass chamber extends in the downstream respiratory gas conduit.

16. The exhalation valve arrangement according to claim 15, wherein a partition that separates the bypass chamber from the downstream respiratory gas conduit is embodied in one piece with the wall that surrounds the downstream respiratory gas conduit.

17. The exhalation valve arrangement according to claim 16, wherein a first exhalation tube that surrounds the upstream respiratory gas conduit, a second exhalation tube that surrounds the downstream respiratory gas conduit, and the partition that separates the bypass chamber from the downstream respiratory gas conduit are embodied in one piece as a conduit component.

18. The exhalation valve arrangement according to claim 1, wherein the valve body is a membrane valve body that spans a longitudinal end of the upstream respiratory gas conduit; and the valve seat is embodied at the longitudinal end of the upstream respiratory gas conduit.

19. The exhalation valve arrangement according to claim 18, wherein the closure encompasses a puncturable closure membrane that is constituted from a material that is softer compared with the material of the encircling sensor attachment wall portion, and
wherein the membrane valve body and the closure membrane are provided with mutually parallel membrane surfaces on the exhalation valve arrangement.

20. The exhalation valve arrangement according to claim 19, wherein when the exhalation valve arrangement is arranged in operationally ready fashion, the closure membrane is arranged orthogonally to the direction of gravity, such that its outer side, facing away from the bypass chamber, faces oppositely to the direction of gravity.

21. The exhalation valve arrangement according to claim 1, wherein the respiratory gas sink comprises external environment.

22. A ventilation apparatus for artificial ventilation of patients, having a respiratory gas supply apparatus from which an inhalation line leads to a patient ventilation interface, from which an exhalation line leads in turn to a respiratory gas sink,
wherein an exhalation valve arrangement according to claim 1 is provided in the exhalation line, the upstream respiratory gas conduit being connected by a portion of the exhalation line to the patient ventilation interface in order to transfer expiratory respiratory gas from the patient ventilation interface.

23. The ventilation apparatus according to claim 22, wherein the respiratory gas sink comprises ambient atmosphere.

* * * * *